(12) United States Patent
Bette

(10) Patent No.: US 6,726,692 B2
(45) Date of Patent: Apr. 27, 2004

(54) ANCILLARY FOR SPINAL OSTEOSYNTHESIS SYSTEM AND PROCESS FOR IMPLANTING A SPINAL OSTEOSYNTHESIS SYSTEM USING THE SAID ANCILLARY

(75) Inventor: Stephane Bette, Paris (FR)

(73) Assignee: Spinevision (FR)

( * ) Notice: Subject to any disclaimer, the term of this patent is extended or adjusted under 35 U.S.C. 154(b) by 0 days.

(21) Appl. No.: 10/205,112

(22) Filed: Jul. 25, 2002

(65) Prior Publication Data
US 2003/0028195 A1 Feb. 6, 2003

(30) Foreign Application Priority Data
Jul. 25, 2001 (FR) .............................. 01 09938

(51) Int. Cl.[7] .......................... A61B 17/58; A61B 17/70
(52) U.S. Cl. .............................. 606/99; 606/61; 81/311
(58) Field of Search .................. 623/17.11; 606/99, 606/61; 81/300, 312, 311

(56) References Cited

U.S. PATENT DOCUMENTS

| 5,020,519 A | * | 6/1991 | Hayes et al. ................. 606/237 |
| 5,364,397 A | * | 11/1994 | Hyes et al. ..................... 606/61 |
| 5,810,878 A | | 9/1998 | Burel et al. |
| 5,910,141 A | | 6/1999 | Morrison et al. |
| 6,478,800 B1 | * | 11/2002 | Fraser et al. .................. 606/99 |

FOREIGN PATENT DOCUMENTS

| FR | 2 677 242 | 12/1992 |
| FR | 2 729 291 | 7/1996 |
| FR | 2 784 571 | 4/2000 |

* cited by examiner

Primary Examiner—Bruce Snow
(74) Attorney, Agent, or Firm—Bachman & LaPointe, P.C.

(57) ABSTRACT

This invention relates to an ancillary for a spinal osteosynthesis system comprising at least one implant that will be implanted in a spine. The implant comprises accommodation means located approximately along a centerline and that will accommodate at least one rod type connecting element. The ancillary comprises holding means that will cooperate with the said implant, and a manipulation means free to move with respect to the said holding means that will be used to manipulate the said connecting element. The said holding means will be arranged on one side of the accommodation means, and the said manipulation means comprises attachment means that will cooperate with the said implant on the side of the centerline of the accommodation means opposite the accommodation means.

Figure 1:
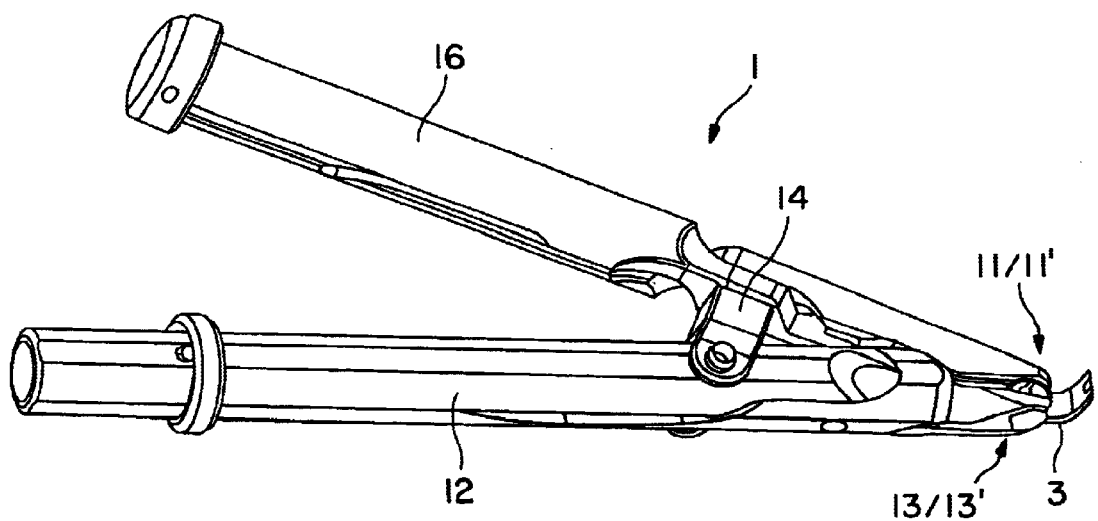

This invention also relates to a process for implantation of a spinal osteosynthesis system comprising at least one implant, using an ancillary.

14 Claims, 6 Drawing Sheets

ANCILLARY FOR SPINAL OSTEOSYNTHESIS SYSTEM AND PROCESS FOR IMPLANTING A SPINAL OSTEOSYNTHESIS SYSTEM USING THE SAID ANCILLARY

This invention relates to the field of ancillaries for spinal osteosynthesis.

This invention relates particularly to an ancillary for a spinal osteosynthesis system of the type comprising at least one implant designed to be implanted in a spine, the said implant comprising accommodation means oriented approximately along an axis and designed to accommodate at least one rod type connecting element, the ancillary comprising holding means intended to cooperate with the said implant and a manipulation means free to move with respect to the said holding means, designed to enable manipulation of the said connecting element.

One of the main difficulties with this type of surgery is placement of the rod in the implants (for example of the hook or pedicular screw type). Another known difficulty is in placing the implant closing system to hold the rod in place in the implant.

Prior art includes ancillaries for spinal osteosynthesis comprising means of holding the rod in place designed to cooperate with the implant.

International patent application No. WO 01/01873 proposes making an ancillary with two spouts that fit into recesses located in the head of the implant, on each side of the accommodation means. The ancillary also comprises a device that is used to exert a force on the rod to move it laterally and/or vertically, to enable positioning of the rod in the accommodation means.

The major disadvantage of ancillaries according to prior art lies in the fact that the implant grip is unilateral, in other words the ancillary only bears on the implant with the holding grip.

The small volume of implants and the fineness of the instrument, which are compulsory for surgical reasons, make it impossible to obtain a very rigid implant grip. The thrust of the rod in the implant requires a variable force depending on the surgical situation, but when large forces are applied, the thrust induces a large torque on the implant, making the implant pivot about the end of the holding grip and possibly tearing off the grips on the implant.

There are two types of consequences; firstly, the implant may no longer be correctly positioned or may be torn off, and secondly the connecting element blocking system may no longer block the connecting element correctly.

This invention is intended to correct the disadvantages of prior art by proposing an ancillary able to distribute the forces exerted on the implant when handling the connecting element so as to minimize the influence of these forces on its positioning.

In order to achieve this, this invention is of the type described above and in its broadest acceptance it is remarkable, in that the said holding means are designed to be arranged on one side of the accommodation means and in that the said manipulation means comprises attachment means that will cooperate with the said implant on the side of the accommodation means opposite the centreline of the accommodation means.

The said manipulation means is preferably fixed removably to the said ancillary.

The said manipulation means is preferably fixed to the said ancillary using a return part enabling free rotation of the said manipulation means.

The ancillary preferably comprises at least one recess to enable the passage of a placement instrument.

The said holding means are preferably located on a lever, with at least a hollow cylindrical part to enable the passage of the said placement instrument.

The said holding means are preferably composed of jaws free to move with respect to each other.

The said attachment means are preferably composed of jaws free to move with respect to each other.

The said jaws, of the said holding means and/or the said attachment means are preferably free to move with respect to each other about a plane of symmetry.

The said hollow cylindrical part is preferably placed such that it has a centreline that passes through the said planes of symmetry of the said jaws.

This invention also relates to a process for installation of a spinal osteosynthesis system comprising at least one implant using an ancillary, the said implant comprising accommodation means arranged approximately along an axis and designed to accommodate at least one rod type connecting element, the ancillary comprising holding means designed to cooperate with the said implant, and a manipulation means free to move with respect to the said holding means, designed to enable manipulation of the said connecting element, in which the said holding means are arranged on one side of the accommodation means, in which the said connecting element is then manipulated using the said manipulation means so that the connecting element centreline is parallel to the centreline of the said accommodation means and in which the said manipulation means comprises attachment means that then cooperate with the said implant on the side of the accommodation means opposite the centreline of the accommodation means.

The said connecting element is preferably located along the centreline of the accommodation means by rotation of the said holding means about a return part.

The said connecting element is preferably located at the bottom of the accommodation means by pushing the connecting element using a placement instrument.

A closing means is then preferably positioned on the said connecting element before withdrawing the said attachment means of the manipulation means and the said holding means.

Advantageously, the ancillary according to the invention forms two clips each fitted with two levers, the two clips being connected together by a return part, the four levers being used to distribute the stresses exerted on each side of the implant, about the means accommodating the connecting element.

Also advantageously, the position of the connecting element is thus easier to make and there is less risk of bad positioning since the stresses applied to the implant are better distributed.

Furthermore, the risk of tearing off the implant is minimised, particularly when the correction applied by the connecting element to the implant once the connecting element positioned in the accommodation means, is high.

Therefore, it is easier and faster to implant an osteosynthesis system using an ancillary according to the invention.

Figure 2:
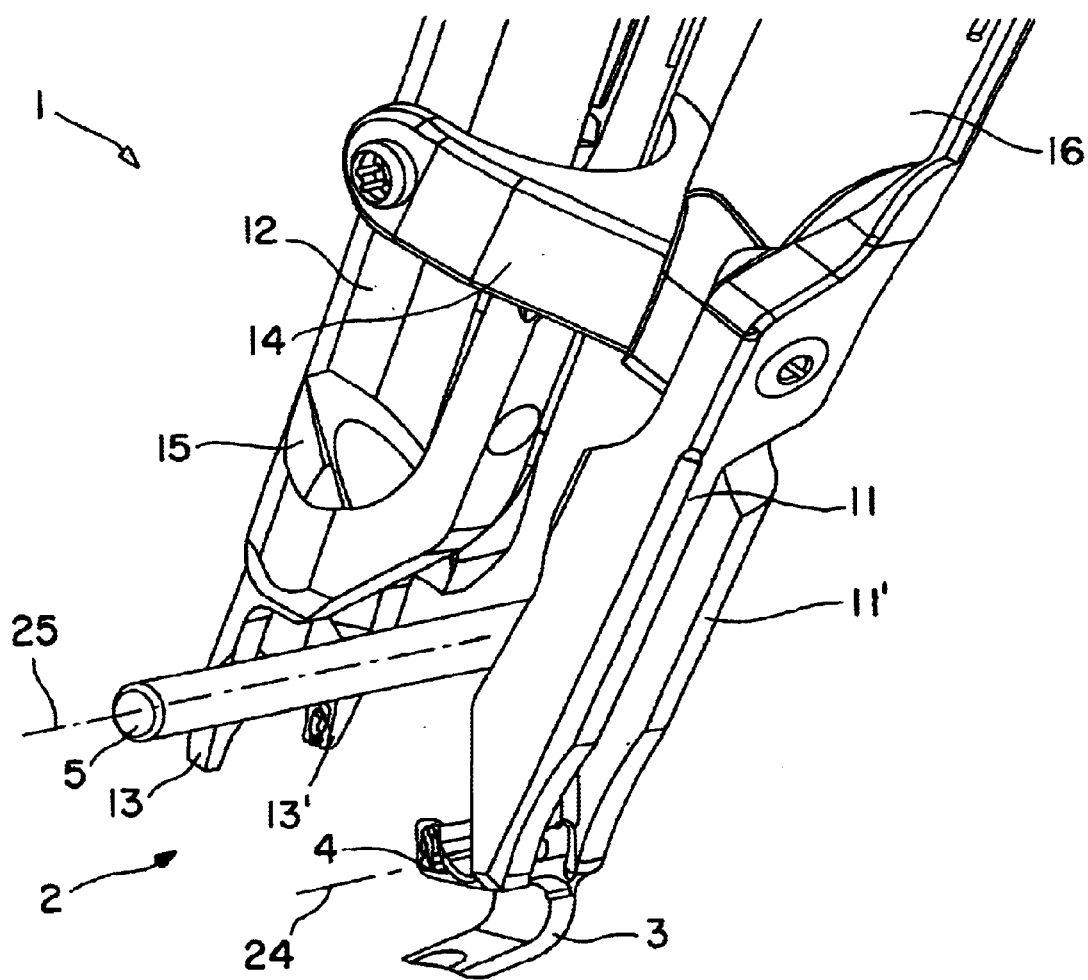
Figure 3:
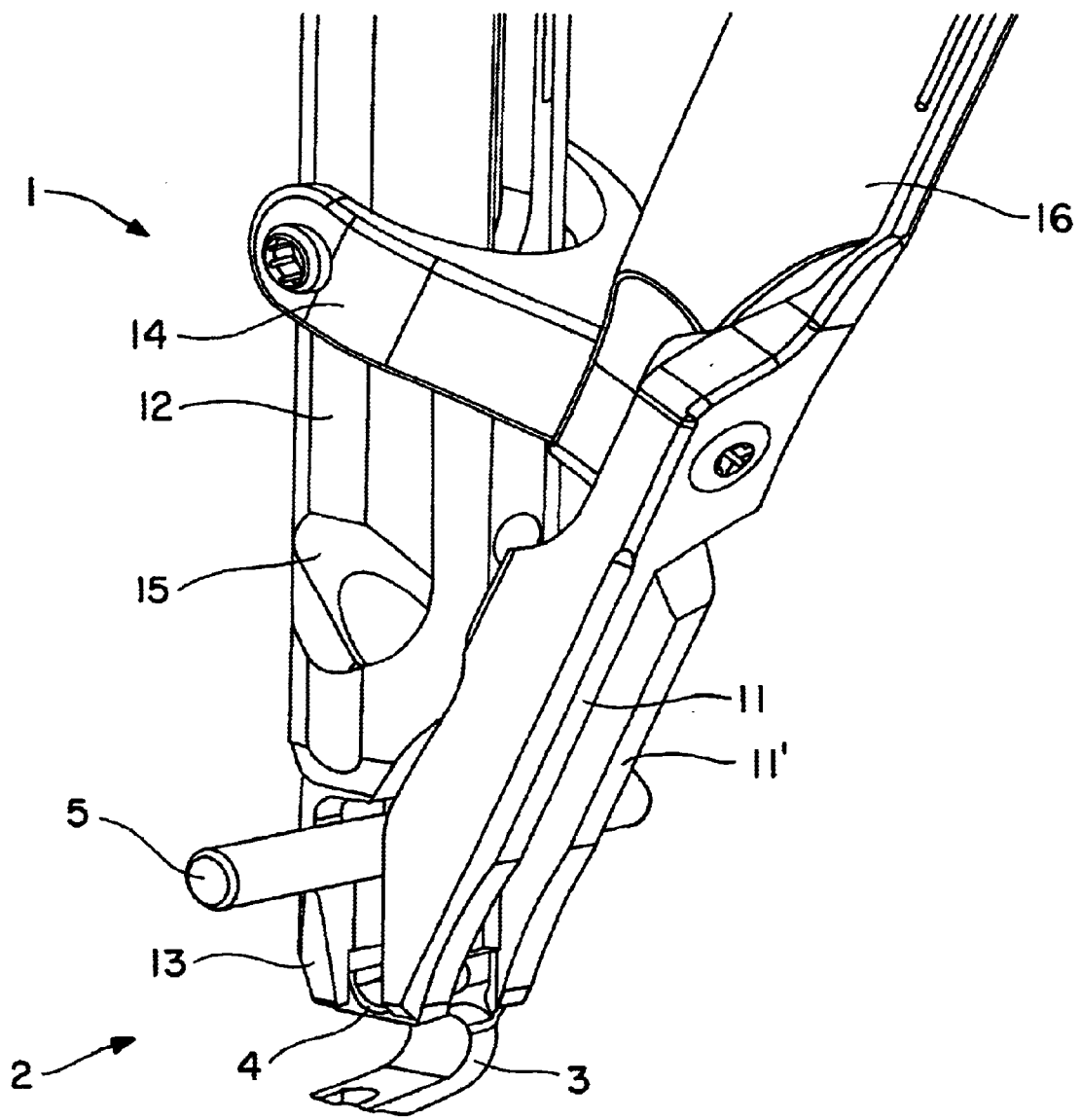
Figure 4:
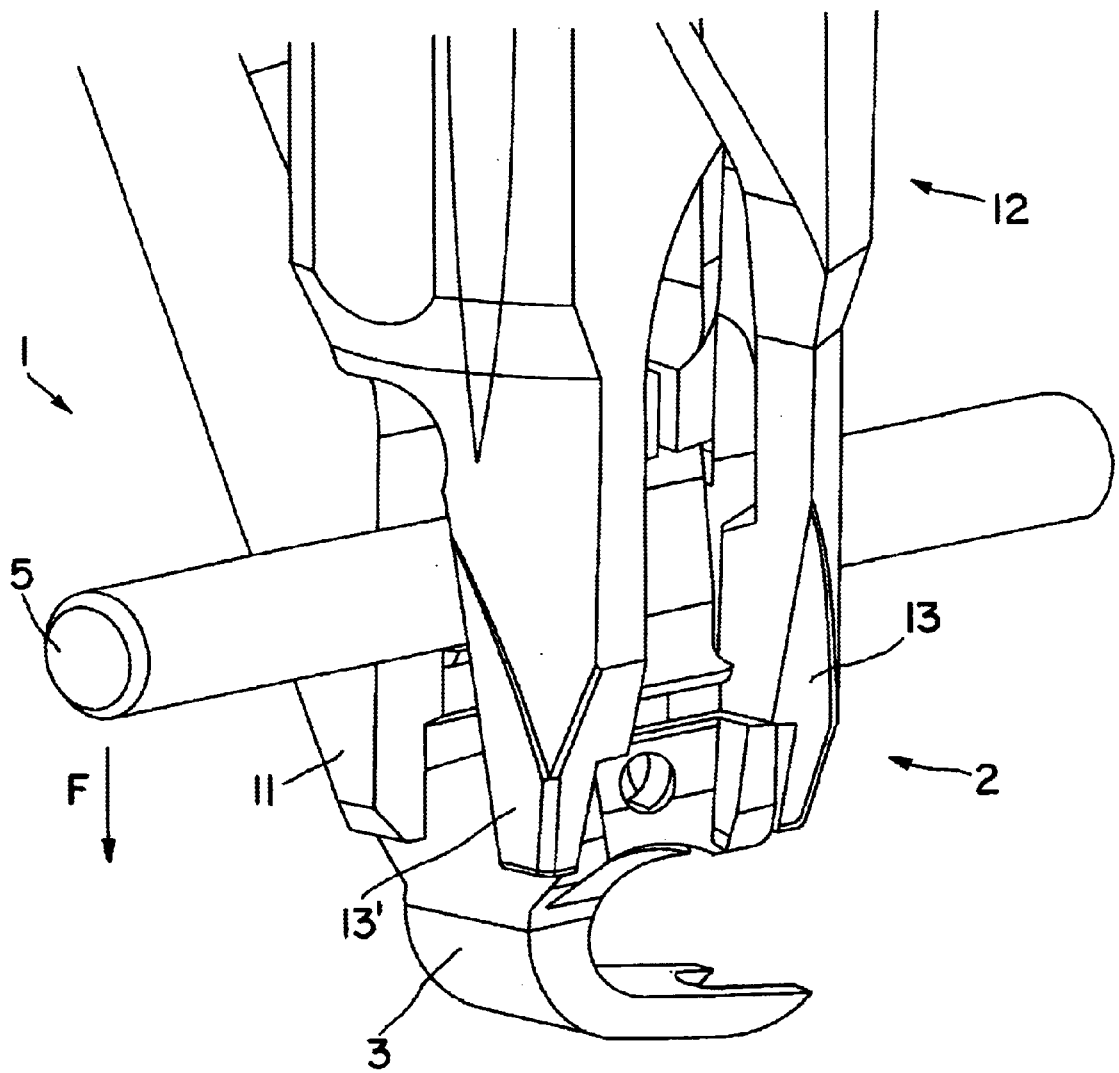
Figure 5:
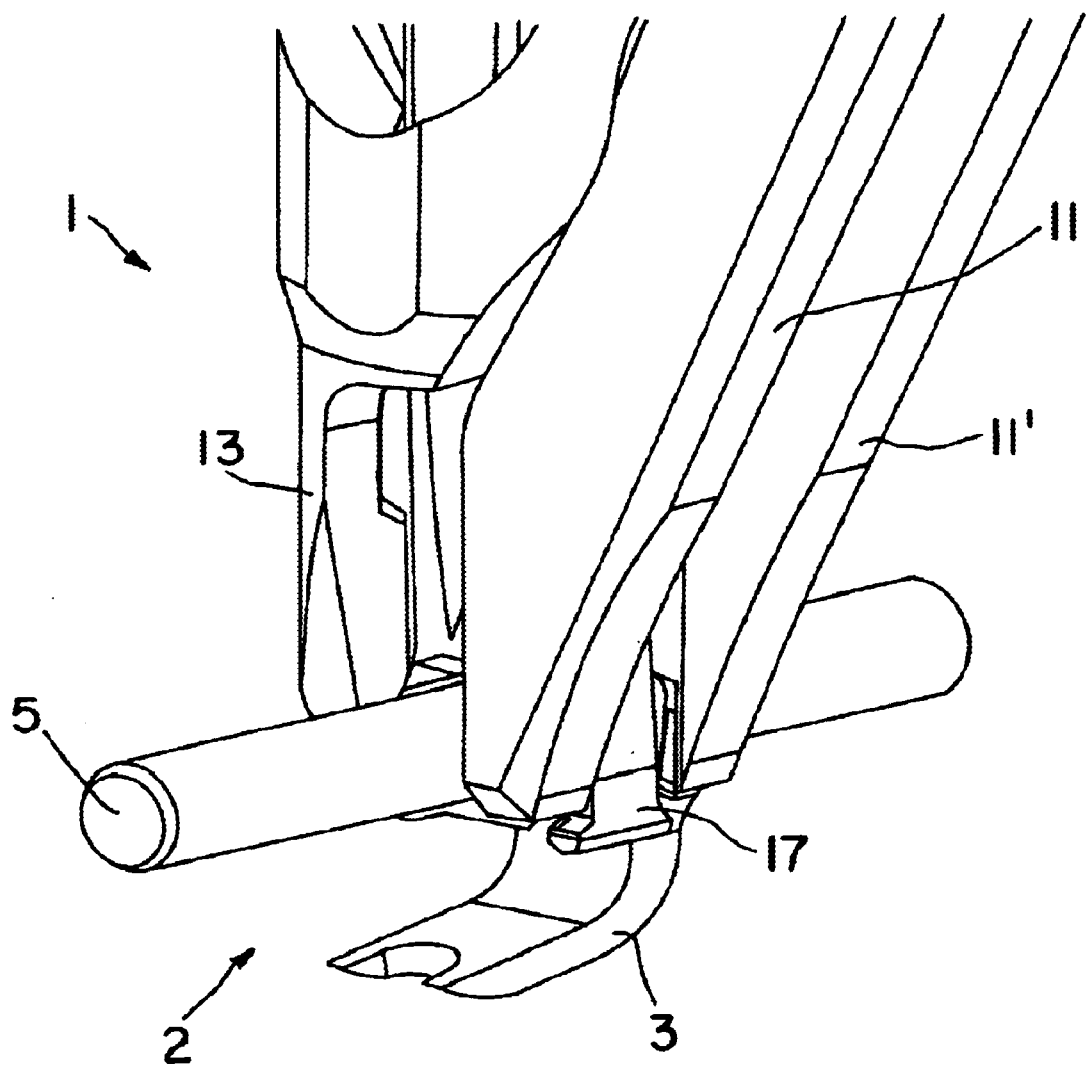
Figure 6:
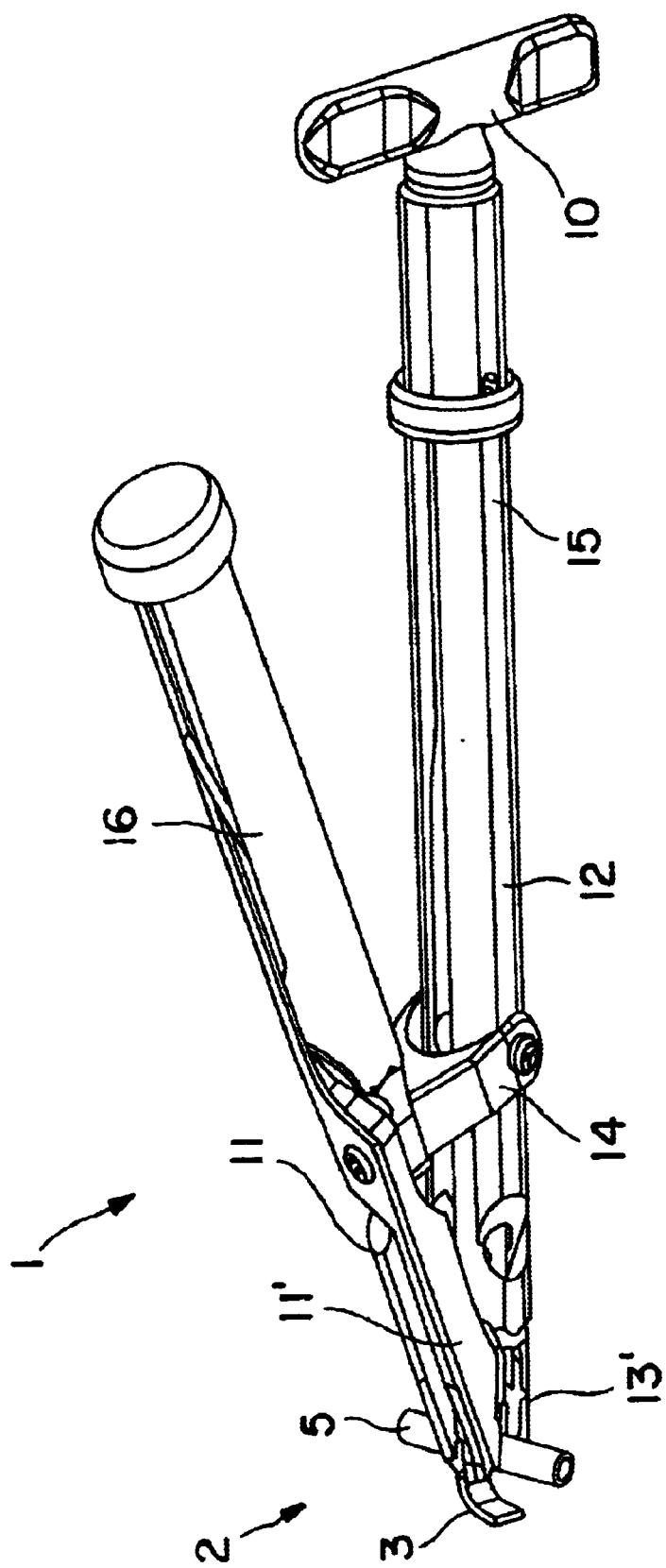

The invention will be better understood after reading the following description of an embodiment of the invention with reference to the attached figures, given solely for explanatory purposes:

FIG. 1 illustrates a perspective view of the ancillary according to the invention and the first manipulation phase of the ancillary according to the invention, FIG. 2 illustrates a partial perspective view of the second manipulation phase of a connecting element using the ancillary according to the invention, FIG. 3 illustrates a partial perspective view of the third manipulation phase of a connecting element using the ancillary according to the invention, FIG. 4 illustrates a partial perspective view opposite the fourth manipulation phase of a connecting element using the ancillary according to the invention, FIG. 5 illustrates a partial perspective view of the fifth manipulation phase of a connecting element using the ancillary according to the invention; and FIG. 6 illustrates a perspective view of the final manipulation position of a connecting element using the ancillary according to the invention.

The ancillary (1) according to the invention illustrated in FIG. 1 is an ancillary for a spinal osteosynthesis system (2). The spinal osteosynthesis system (2) shown in FIG. 2 comprises at least one implant (3) that will be implanted in a spine and at least one rod type connecting element (5) with a centreline (25). The said implant (3) comprises accommodation means (4) approximately along at least one centreline (24) and that will accommodate the connecting element (5).

For example, the implant (3) may be of the type divulged in international patent application No. WO 01/01873.

The ancillary (1) comprises holding means (11, 11') that will cooperate with the said implant (3) and a manipulation means (12) free to move with respect to the said holding means (11, 11'), that will be used to manipulate the said connecting element (2).

The holding means (11, 11') thus form a holding grip (16) and the attachment means (13, 13') form a manipulation grip, the two grips of the ancillary being hinged to each other. These two grips may possibly be completely separated from each other.

The said holding means (11, 11') will be arranged on one side of the accommodation means (4) and the said manipulation means (12) comprises attachment means (13, 13') that will cooperate with the said implant (3) on the side of the accommodation means (4) opposite the centreline (24) of the accommodation means.

Thus, when the manipulation lever used to manipulate the connecting element comes close to the implant, it may be attached to the implant such that the forces subsequently transmitted by the ancillary onto the implant pass through the two levers of the grip and do not modify the position of the implant, and do not tear it off.

The said holding means (11, 11') that will be used to keep the holding grip (16) in place on the implant (3) and the said attachment means (13, 13') that will be used to attach the manipulation lever to the implant (3) are composed of a pair of jaws each. Each jaw in each pair is free to move with respect to the other jaw.

The said holding means (11, 11') and the said attachment means (13, 13') may possibly be composed of hooks that will cooperate with complementary shapes formed on the implant (3).

In each pair of holding means (11, 11') and attachment means (13, 13'), the said jaws are free to move with respect to the other about a plane of symmetry, in other words the jaws are provided with connecting means such that when one jaw is moved by a given distance with respect to the central position, the other jaw moves by the same distance with respect to this central position.

Thus the ancillary (1) according to the invention forms a pair of grips with two levers each, the four levers being free to move with respect to each other in pairs and each lever comprises one jaw.

The ancillary according to the invention is composed of two grips, the first representing the holding means and the second representing the manipulation means. The manipulation grip is only fixed to the said implant and only after the connecting element has been aligned in the accommodation means, in other words when the centreline (25) of the connecting element (5) is parallel to the centreline (24) of the said accommodation means (4).

The manipulation means (12) is fixed to the said holding means forming the ancillary (1) using a return part (14) that enables free rotation of the said manipulation means (12). This return part is composed of a basic rod fixed to the holding grip (16) and a semi-circular arc shaped part with an inside diameter approximately equal to the outside diameter of the manipulation means (12). The ends of this arc shape are provided with slits, or holes each of which cooperates with a stud or a pin or a screw fixed on each side of the manipulation means (12).

If the manipulation means is fixed removably, the return part (14) comprises slits at the end of its arc shape that will cooperate with a stud or a pin or a screw fixed on each side of the manipulation means (12). If the manipulation means is fixed non removably, the return part comprises holes at the end of its arc shape, each of which will cooperate with a stud or a pin or with a screw fixed on each side of the manipulation means (12).

Thus, the return part (14) enables rotation of the said manipulation element until the jaws are aligned with the implant attachment means. Similarly, this rotation of the manipulation element will align the connecting element with the implant accommodation means.

The ancillary (1) also comprises at least one recess in the centreline of the implant to enable a placement instrument (10) to pass, in order to push the connecting element (5) to the bottom of the accommodation means (4) without needing to remove the ancillary (1).

In a preferred version, this recess is formed by at least one hollow cylindrical part (16) located on the manipulation lever (12) as illustrated in FIG. 6 and through which the placement instrument (10) can pass.

The manipulation lever (12) preferably has at least one hollow cylindrical part (15) throughout its full thickness.

The hollow cylindrical part(s) (15) is or are positioned such that it (they) has (have) a single axis that passes through the said planes of symmetry of the said jaws.

Thus, when the ancillary according to the invention is being used, the first step is to temporarily fix the holding grip (16) of the ancillary onto the implant using the holding means (11, 11') as illustrated in FIG. 1. During this first phase, the jaws of the holding means (11, 11') are closed onto the sidewalls of the implant (3), on the same side of the centreline of the accommodation means as the accommodation means (4). It is important that the jaws of the holding means (11, 11') do not project into the area of the accommodation means (4) that are reserved for the connecting element (5), to avoid hindering insertion of the connecting element (5) into the accommodation means (4).

FIG. 2 illustrates the phase in which the connecting element is moved towards the accommodation means (4) of the implant. If the manipulation means or lever (12) is not connected to the holding grip (16), it may be more practical to attach the holding grip (16) to the manipulation lever to form the grip, only after this approach phase. During this approach phase, the centreline of the connecting element (5) may not necessarily be parallel to the centreline of the accommodation means (4).

The third phase illustrated in FIG. 3 consists of pushing on the connecting element (5) using the manipulation lever (12) so that the centreline (25) of the connecting element (5)

becomes parallel to the centreline (24) of the accommodation means (4).

At the end of this third phase, the jaws of the attachment means (13, 13') are closed in contact with the sidewalls of the implant (3) on the side of the holding means (12) opposite to the centreline (24) of the accommodation means. It is important that the jaws of the attachment means (13, 13') do not project into the space of the accommodation means (4) for use by the connecting element (5).

The fourth phase illustrated in FIG. 4 consists of pushing the connecting element (5) along the direction of the arrow F to position it in the accommodation means (4).

FIG. 5 illustrates the state of the osteosynthesis system when the connecting element (5) is positioned in the accommodation means (4).

To fix the connecting element (5) effectively in the implant (3), the next step is then to use a closing means (17) designed effectively to cooperate with the implant (3) to enable the connecting element (5) to be blocked in the accommodation means (4) as illustrated in FIG. 5.

In the example illustrated, this closing means (17) is a clip that is clipped into place using the placement instrument (10) as illustrated in FIG. 6.

This instrument was firstly inserted into the cylindrical part (15) of the manipulation means (12). It is free to rotate and is guided perfectly in this cylindrical part (16).

The said connecting element (5) may also be positioned at the bottom of the accommodation means (4) by pushing the connecting element using the closing means (17) installed on the placement instrument (10).

The invention is described above by way of example. Obviously, those skilled in the art will be capable of making different variants of the invention without departing from the scope of the patent.

What is claimed is:

1. An ancillary for a spinal osteosynthesis system comprising:
   holding means for cooperating with an implant having an accommodation means, said holding means comprising a pair of holding elements for holding said implant in a desired position;
   said holding elements being arranged on a first side of said implant accommodation means and at least one of the holding elements being movable with respect to another of said holding elements;
   manipulation means for manipulating a connecting element to place said connecting element in said accommodation means, said manipulation means being free to move with respect to said holding means; and
   said manipulation means having attachment means for cooperating with said implant, said attachment means being located on a second side of said accommodation means.

2. An ancillary according to claim 1, wherein said manipulation means is removably fixed to said ancillary.

3. An ancillary according to claim 1, wherein said manipulation means is fixed to the ancillary by a return part which enables free rotation of the manipulation means.

4. An ancillary according to claim 1, further comprising a recess for receiving and enabling a placement instrument to push the connecting element to a bottom of the accommodation means.

5. An ancillary according to claim 4, wherein said recess comprises a hollow cylindrical part for passage of the placement instrument.

6. An ancillary according to claim 1, wherein the holding elements comprise a pair of jaws free to move with respect to one another.

7. An ancillary according to claim 6, wherein said jaws are free to move with respect to each other with respect to a plane of symmetry.

8. An ancillary according to claim 1, wherein said attachment means comprises a pair of jaws free to move with respect to each other.

9. An ancillary according to claim 8, wherein said jaws are free to move with respect to each other with respect to a plane of symmetry.

10. An ancillary according to claim 9, further comprising a hollow cylindrical part having a centerline and said hollow cylindrical part being positioned such that said centerline passes through said plane of symmetry.

11. A process for implanting a spinal osteosynthesis system comprising the steps of:
   providing an implant having an accommodation means located approximately along a centreline and a connecting element to be seated in said accommodation means;
   providing an ancillary having a pair of holding elements for holding said implant in a desired position, which holding elements are arranged on a first side of the accommodation means and are arranged so that at least one holding element is movable with respect to the other holding element, manipulation means for manipulating said connecting element, and said manipulation means having attachment means for cooperating with said implant, said attachment means being located on a second side of said accommodation means;
   holding said implant on said first side of said accommodation means with said holding elements; and
   manipulating the connecting element using said manipulation means so that a centreline of the connecting element becomes parallel to a centreline of said accommodation means.

12. A process according to claim 11, further comprising placing said connecting element on the centerline of said accommodation means by rotating said holding elements about a return part.

13. A process according to claim 11, further comprising placing said connecting element a bottom of the accommodation means by pushing the connecting element with a placement instrument.

14. A process according to claim 11, further comprising positioning a closing means on the connecting element before the attachment means are withdrawn from the manipulation means and the holding elements.

* * * * *